United States Patent [19]

Stahl et al.

[11] Patent Number: 5,470,952
[45] Date of Patent: Nov. 28, 1995

[54] CNTF AND IL-6 ANTAGONISTS

[75] Inventors: Neil Stahl, Carmel; Aris N. Economides, New York; George D. Yancopoulos, Yorktown Heights, all of N.Y.

[73] Assignee: Regeneron Pharmaceuticals, Inc., Tarrytown, N.Y.

[21] Appl. No.: 140,222

[22] Filed: Oct. 20, 1993

[51] Int. Cl.⁶ .................................................. C07K 14/475
[52] U.S. Cl. ........................ 530/350; 530/351; 530/399; 530/402; 424/85.2
[58] Field of Search ................................... 530/350, 351, 530/399; 424/85.2; 930/147

[56] References Cited

PUBLICATIONS

Baumann et al. (Apr. 24, 1993) *J. Biol. Chem.* 268:8414.
Davis et al. (Jun. 18, 1993) *Science* 260:1805.
Ip et al. (Jun. 26, 1992) *Cell* 69:1121.
Kishimoto et al. (Oct. 23, 1992) 258:593.
Murakami et al. (Jun. 18, 1993) *Science* 260:1808.
Stahl et al. (Apr. 15, 1993) *J. Biol. Chem.* 268:7628.
Stahl et al. (Aug. 27, 1993) *Cell* 74:587.
Devos et al. (1991) The EMBO J. 10:2133–2137.

*Primary Examiner*—Garnette D. Draper
*Assistant Examiner*—Shelly Guest Cermak
*Attorney, Agent, or Firm*—Gail M. Kempler

[57] ABSTRACT

Heterodimer proteins comprising a soluble α specificity determining cytokine receptor component and the extracellular domain of a β receptor component function as CNTF and IL-6 antagonsists.

2 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown     ( i i ) MOLECULE TYPE: peptide     ( x i ) SEQUENCE DESCRIPTION: SEQ ID NO:1:

His His His His His His
    1                5

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown     ( i i ) MOLECULE TYPE: peptide     ( x i ) SEQUENCE DESCRIPTION: SEQ ID NO:2:

Cys Gly Thr Glu Gly Gln Val Glu Arg Phe Glu Thr Val Gly Met Glu
    1            5                      10                  15

CNTF AND IL-6 ANTAGONISTS

BACKGROUND OF THE INVENTION

Although discovered for varying biological activities, ciliary neurotrophic factor (CNTF), leukemia inhibitory factor (LIF), oncostatin M (OSM) and interleukin-6 (IL-6) comprise a newly defined family of cytokines (referred to herein as the "CNTF family" of cytokines). These cytokines are grouped together because of their distant structural similarities [Bazan, J. Neuron 7:197–208 (1991); Rose and Bruce, Proc. Natl. Acad. Sci. USA 88:8641–8645 (1991)], and, perhaps more importantly, because they share "13" signal-transducing receptor components [Baumann, et al., J. Biol. Chem. 265:19853–19862 (1993); Davis, et al., Science 260:1805–1808 (1993); Gearing et al., Science 255:1434–1437 (1992); Ip et al., Cell 69:1121–1132 (1992); Stahl, et al., J. Biol. Chem. 268:7628–7631 (1993); Stahl and Yancopoulos, Cell 74:587–590 (1993)]. Receptor activation by this family of cytokines results from either homo- or hetero-dimerization of these 13 components [Davis, et al. Science 260:1805–1808 (1993), Murakami, et al., Science 260:1808–1810 (1993); Stahl and Yancopoulos, Cell 74:587–590 (1993)]. IL-6 receptor activation requires homodimerization of gp130 [Murakami, et al. Science 260:1808–1810 (1993), Hibi, et al., Cell 63: 1149–1157 (1990)], a protein initially identified as the IL-6 signal transducer [Hibi, et al., Cell 63:1149–1157 (1990)]. CNTF, LIF and OSM receptor activation results from heterodimerization between gp130 and a second gp130-related protein known as LIFRIβ [Davis, et al., Science 260:1805–1808 (1993)], that was initially identified by its ability to bind LIF [Gearing et al., EMBO J. 10:2839–2848 (1991)].

In addition to the β components, some of these cytokines also require specificity-determining "α" components that are more limited in their tissue distribution than the β components, and thus determine the cellular targets of the particular cytokines [Stahl and Yancopoulos, Cell 74:587–590 (1993)]. Thus, LIF and OSM are broadly acting factors that may only require the presence of gp130 and LIFRβ on responding cells, while CNTF requires CNTFRα [Stahl and Yancopoulos, Cell 74:587–590 (1993)] and IL-6 requires IL-6Rα [Kishimoto, et al., Science 258:593–597 (1992)]. Both CNTFRα (Davis et al., Science 259:1736–1739 (1993) and IL-6Rα [Hibi, et al. Cell 63:1149–1157, Murakami et al., Science 260:1808–1810 (1990); Taga, et al., Cell 58:573–581 (1989)] can function as soluble proteins, consistent with the notion that they do not interact with intercellular signaling molecules but that they serve to help their ligands interact with the appropriate signal transducing β subunits [Stahl and Yancopoulos, Cell 74:587–590 (1993)].

Additional evidence from other cytokine systems also supports the notion that dimerization provides a common mechanism by which all cytokine receptors initiate signal transduction. Growth hormone (GH) serves as perhaps the best example in this regard. Crystallographic studies have revealed that each GH molecule contains two distinct receptor binding sites, both of which are recognized by the same binding domain in the receptor, allowing a single molecule of GH to engage two receptor molecules [de Vos, et al., Science 255:306–312 (1992)]. Dimerization occurs sequentially, with site 1 on the GH first binding to one receptor molecule, followed by the binding of site 2 to a second receptor molecule [Fuh, et al., Science 256:1677–1680 (1992)]. Studies with the erythropoietin (EPO) receptor are also consistent with the importance of dimerization in receptor activation, as EPO receptors can be constitutively activated by a single amino acid change that introduces a cysteine residue and results in disulfide-linked homodimers [Watowich, et al., Proc. Natl. Acad. Sci. USA 89:2140–2144 (1992)].

Figure 1:
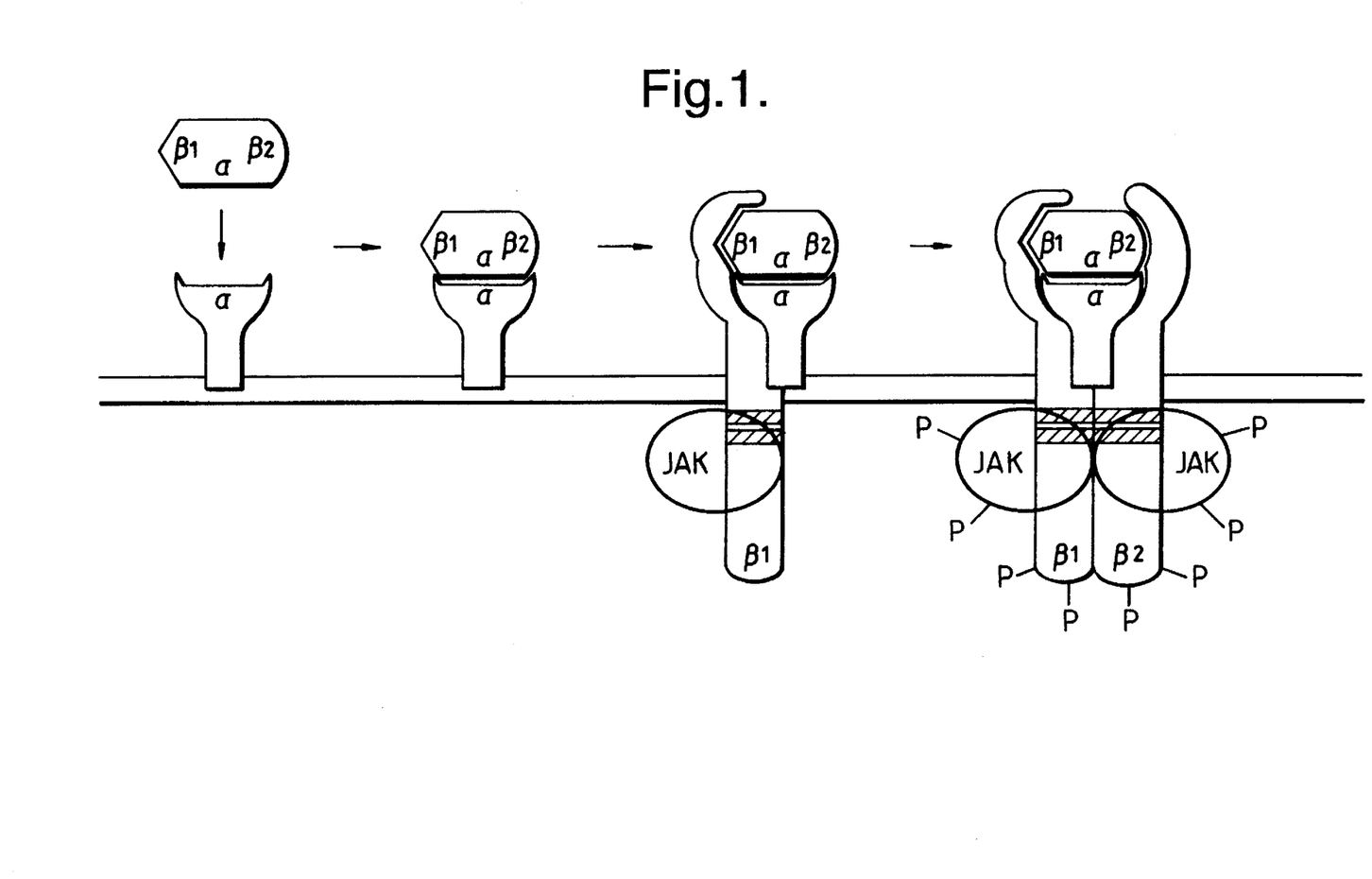
FIG. 1: Ordered binding of receptor components in a model of a generic cytokine receptor. The model indicates that cytokines contain up to 3 receptor binding sites and interact with their receptor components by binding first the optional a component, followed by binding to $\beta1$, and then $\beta2$. The $\beta$ components for many cytokine receptors interact through membrane proximal regions (shaded boxes) with the Jak/Tyk family of cytoplasmic protein tyrosine kinases. Only upon dimerization of $\beta$ components is signal transduction initiated, as schematized by the tyrosine phosphorylations (P) of the $\beta$ components and the Jak/Tyk kinases.

In addition to homo- or hetero-dimerization of β subunits as the critical step for receptor activation, a second important feature is that formation of the final receptor complex by the CNTF family of cytokines occurs through a mechanism whereby the ligand successively binds to receptor components in an ordered manner [Davis, et al. Science 260:1805–1818 (1993); Stahl and Yancopoulos, Cell 74:587–590 (1993)]. Thus CNTF first binds to CNTFRα, forming a complex which then binds gp130 to form an intermediate (called here the αβ1 intermediate) that is not signaling competent because it has only a single β component, before finally recruiting LIFRβ to form a heterodimer of β components which then initiates signal transduction. Although a similar intermediate containing IL-6 bound to IL-6Rα and a single molecule of gp130 has not been directly isolated, we have postulated that it does exist by analogy to its distant relative, CNTF, as well as the fact that the final active IL-6 receptor complex recruits two gp130 monomers. Altogether, these findings led to a proposal for the structure of a generic cytokine receptor complex (FIG. 1) in which each cytokine can have up to 3 receptor binding sites: a site that binds to an optional α specificity-determining component (α site), a site that binds to the first β signal-transducing component (β1 site), and a site that binds to the second β3 signal-transducing component (β2 site)[Stahl and Yancopoulos, Cell 74:587–590 (1993)]. These 3 sites are used in sequential fashion, with the last step in complex formation—resulting in β component dimerization—critical for initiating signal transduction [Davis, et al. Science 260:1805–1818 (1993)]. Knowledge of the details of receptor activation and the existence of the non-functional β1 intermediate for CNTF has led to the finding that CNTF is a high affinity antagonist for IL-6 under certain circumstances, and provides the strategic basis for designing ligand or receptor-based antagonists for the CNTF family of cytokines as detailed below.

Once cytokine binding induces receptor complex formation, the dimerization of β components activates intracellular tyrosine kinase activity that results in phosphorylation of a wide variety of substrates [Ip, et al. Cell 69:121–1132 (1992)]. This activation of tyrosine kinase appears to be critical for downstream events since inhibitors that block the tyrosine phosphorylations also prevent later events such as gene inductions [Ip, et al., Cell 69:121–1132 (1992); Nakajima and Wall, Mol. Cell. Biol. 11:1409–1418 (1991)]. Recently, we have demonstrated that a newly discovered family of non-receptor tyrosine kinases that includes Jak1, Jak2, and Tyk2 (referred to as the Jak/Tyk kinases) [Firmbach-Kraft, et al., Oncogene 5:1329–1336 (1990); Wilks, et al., Mol. Cell. Biol. 11:2057– 2065 (1991] and that are involved in signal transduction with other cytokines [, et al., Cell 74:237–244 (1993); Silvennoinen, et al., Proc. Natl. Acad. Sci. USA (in press; 1993); Velazquez, et al., Cell 70:313–322 (1992); Witthuhn, et al., Cell 74:227–236 (1993)], preassociate with the cytoplasmic domains of the β subunits gp130 and LIFRβ in the absence of ligand, and become tyrosine phosphorylated and activated upon ligand addition [Stahl et al., Science (submitted; 1993)]. Therefore these kinases appear to be the most proximal step of intracellular signal transduction activated inside the cell as a result of ligand binding outside of the cell. Assay systems for screening collections of small molecules for specific agonist or antagonist activities based on this system are described below.

The CNTF family of cytokines play important roles in a wide variety of physiological processes that provide potential therapeutic applications for both antagonists and agonists.

SUMMARY OF THE INVENTION

An object of the present invention is the production of IL-6 antagonists that are useful in the treatment of IL-6 related diseases or disorders.

Another object of the invention is the use of IL-6 antagonists described herein for the treatment of osteoporosis.

Another object of the invention is the use of IL-6 antagonists described herein for the treatment of both the primary and second effects of cancers, including multiple myeloma.

Yet another object of the invention is the use of IL-6 antagonists described herein for the treatment of cachexia.

Another object of the invention is the development of screening systems useful for identifying novel agonists and antagonists of members of the CNTF family of cytokines.

Another object of the invention is the development of screening systems useful for identifying small molecules that act as agonists or antagonists of the CNTF family of cytokines.

These and other objects are achieved by the use of CNTF family receptor components to produce nonfunctional intermediates which have both therapeutic activity as IL-6 and CNTF antagonists, as well as utility in assay systems useful for identifying novel agonists and antagonists of the CNTF cytokine family members.

DETAILED DESCRIPTION OF THE INVENTION

The present invention provides novel antagonists which are based on receptor components that are shared by cytokines such as the CNTF family of cytokines.

The invention described herein contemplates the production of antagonists to any cytokine that utilizes an $\alpha$ specificity determining component which, when combined with the cytokine, binds to a first $\beta$ signal transducing component to form a nonfunctional intermediate which then binds to a second $\beta$ signal transducing component causing $\beta$-receptor dimerization and consequent signal transduction. According to the invention, the soluble $\alpha$ specificity determining component of the receptor (sR$\alpha$) and the extracellular domain of the first $\beta$ signal transducing component of the cytokine receptor ($\beta1$) are combined to form heterodimers (sR$\alpha$:$\beta1$) that act as antagonists to the cytokine by binding the cytokine to form a nonfunctional complex.

As described in Example 1, CNTF and IL-6 share the $\beta1$ receptor component gp130. The fact that CNTF forms an intermediate with CNTFR$\alpha$ and gp130 can be demonstrated (Example 1) in cells lacking LIFR$\beta$, where the complex of CNTF and CNTFR$\alpha$ binds gp130, and prevents homodimerization of gp130 by IL-6 and IL-6R$\alpha$, thereby blocking signal transduction. These studies provide the basis for the development of the IL-6 antagonists described herein, as they show that if, in the presence of a ligand, a nonfunctional intermediate complex, consisting of the ligand, its $\alpha$ receptor component and its $\beta1$ receptor component, can be formed, it will effectively block the action of the ligand. Other cytokines may use other $\beta1$ receptor components, such as LIFR$\beta$, which may also be used to produce antagonists according to the present invention.

Thus for example, in one embodiment of the invention, effective antagonists of IL-6 or CNTF consist of heterodimers of the extracellular domains of the $\alpha$ specificity determining components of their receptors (sIL-6R$\alpha$ and sCNTFR$\alpha$ respectively) and the extracellular domain of gp130. The resultant heterodimers, which are referred to hereinafter as sIL-6R$\alpha$:$\beta1$ and sCNTFR$\alpha$:$\beta1$ respectively, function as high-affinity traps for IL-6 or CNTF, respectively, thus rendering the cytokine inaccessible to form a signal transducing complex with the native membrane-bound forms of their receptors.

Although soluble ligand binding domains from the extracellular portion of receptors have proven to be somewhat effective as traps for their ligands and thus act as antagonists [Bargetzi, et al., Cancer Res. 53:4010–4013 (1993);, et al., Proc. Natl. Acad. Sci. USA 89:8616– 8620 (1992); Mohler, et al., J. Immunol. 151:1548–1561 (1993); Narazaki, et al., Blood 82:1120–1126 (1993)], the IL-6 and CNTF receptors are unusual in that the $\alpha$ receptor components constitute ligand binding domains that, in concert with their ligands, function effectively in soluble form as receptor agonists [Davis, et al. Science 259:1736–1739 (1993); Taga, et al., Cell 58:573– 581 (1989)]. The sR$\alpha$:$\beta1$ heterodimers prepared according to the present invention provide effective traps for their ligands, binding these ligands with affinities in the picomolar range (based on binding studies for CNTF to PC12D cells) without creating functional intermediates.

The $\alpha$ and $\beta$ receptor extracellular domains may be prepared using methods known to those skilled in the art. The CNTFR$\alpha$ receptor has been cloned, sequenced and expressed [Davis, et al. (1991) Science 253:59–63 which is incorporated by reference in its entirety herein]. The cloning of LIFR$\beta$60 and gp130 are described in Gearing et al. in EMBO J. 10:2839–2848 (1991), Hibi, et al. Cell 63:1149–1157 (1990) and in published PCT application WO 93/10151 published May 27, 1993, all of which are incorporated by reference in their entirety herein.

The receptor molecules useful for practicing the present invention may be prepared by cloning and expression in a prokaryotic or eukaryotic expression system. The recombinant receptor gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The sRα:β heterodimeric receptors may be engineered using known fusion regions, as described in published PCT application WO 93/10151 published May 27, 1993 entitled "Receptor for Oncostatin M and Leukemia Inhibitory Factor" which describes production of β receptor heterodimers, or they may be prepared by crosslinking of extracellular domains by chemical means. The domains utilized may consist of the entire extracellular domain of the α and β components, or they may consist of mutants or fragments thereof that maintain the ability to form a complex with its ligand and other components in the sRα:β1 complex.

In one embodiment of the invention, the extracellular domains are engineered using leucine zippers. The leucine zipper domains of the human transcription factors c-jun and c-fos have been shown to form stable heterodimers [Busch and Sassone-Corsi, Trends Genetics 6:36–40 (1990); Gentz, et al., Science 243:1695–1699 (1989)] with a 1:1 stoichiometry. Although jun-jun homodimers have also been shown to form, they are about 1000-fold less stable than jun-fos heterodimers. Fos-fos homodimers have not been detected.

The leucine zipper domain of either c-jun or c-fos are fused in frame at the C-terminus of the soluble or extracellular domains of the above mentioned receptor components by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His-His-His-His-His-His (His6), [Seq.ID. No.1] to allow rapid purification by metal-chelate chromatography, and/or by epitopes to which antibodies are available, to allow for detection on western blots, immunoprecipitation, or activity depletion/blocking in bioassays.

In another embodiment, the sRα:β1 heterodimer is prepared using a similar method, but using the Fc-domain of human IgG1 [Aruffo, et al., Cell 67:35–44 (1991)]. In contrast to the latter, formation of heterodimers must be biochemically achieved, as chimeric molecules carrying the Fc-domain will be expressed as disulfide-linked homodimers. Thus, homodimers may be reduced under conditions that favor the disruption of inter-chain disulfides but do not effect intra-chain disulfides. Then monomers with different extracellular portions are mixed in equimolar amounts and oxidized to form a mixture of homo- and heterodimers. The components of this mixture are separated by chromatographic techniques. Alternatively, the formation of this type of heterodimers may be biased by genetically engineering and expressing molecules that consist of the soluble or extracellular portion of the receptor components followed by the Fc-domain of hIgG, followed by either the c-jun or the c-fos leucine zippers described above [Kostelny, et al., J. Immunol. 148:1547–1553 (1992)]. Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In another embodiment of the invention the sRα:β1 heterodimers are prepared by expression as chimeric molecules utilizing flexible linker loops. A DNA construct encoding the chimeric protein is designed such that it expresses two soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the order of the soluble or extracellular domains fused is switched (e.g. sIL6Rα/loop/sgp130 or sgp130/loop/sIL-6Rα) and/or in which the length and composition of the loop is varied, to allow for selection of molecules with desired characteristics.

Alternatively, the heterodimers made according to the present invention may be purified from cell lines cotransfected with the appropriate α and β components. Heterodimers may be separated from homodimers using methods available to those skilled in the art. For example, limited quantities of heterodimers may be recovered by passive elution from preparative, nondenaturing polyacrylamide gels. Alternatively, heterodimers may be purified using high pressure cation exchange chromatography. Excellent purification has been obtained using a Mono S cation exchange column.

In addition to sRα:β1 heterodimers that act as antagonists by binding free CNTF or IL-6, the present invention also contemplates the use of engineered, mutated versions of IL-6 with novel properties that allow it to bind to IL-6Rα and a single gp130 molecule, but fail to engage the second gp130 to complete β component homodimerization, and thus act as an effective IL-6 antagonist on any IL-6 responsive cell. Our model for the structure of the IL-6 and CNTF receptor complexes indicates that these cytokines have distinct sites for binding the α, β1, and β2 receptor components [Stahl and Yancopoulos, Cell 74:587–590 (1993)]. Mutations of critical amino acid residues comprising each of these sites gives rise to novel molecules which have the desired antagonistic properties. Ablation of the β1 site would give a molecule which could still bind to the α receptor component but not the β1 component, and thereby comprise an antagonist with nanomolar affinity. Mutations of critical amino acid residues comprising the β2 site of IL-6 (IL-6132-) would give a molecule that would bind to IL-6Rα and the first gp130 monomer, but fail to engage the second gp130 and thus be functionally inactive. Similarly, mutations of the CNTF β2 site would give a molecule (CNTFβ2-) that would bind CNTFRα and gp130, but fail to engage LIFRβ, thereby antagonizing CNTF action by forming the nonfunctional β1 intermediate. Based on the binding results described above where CNTF forms the β1 intermediate with high affinity, both CNTFβ2- and IL-6β2- would constitute antagonists with affinity in the range of 10 pM.

A variety of means are used to generate and identify mutations of IL-6 or CNTF that have the desired properties. Random mutagenesis by standard methods of the DNA encoding IL-6 or CNTF may be used, followed by analysis of the collection of products to identify mutated cytokines having the desired novel properties as outlined below. Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells (1989), Science 244: 1081–1085] and homolog-scanning mutagenesis [Cunningham, et al., (1989), Science 243:1330–1336].

Targeted mutagenesis of the IL-6 or CNTF nucleic acid sequences using such methods can be used to generate CNTFβ2- or IL-6β2- candidates. The choice of regions appropriate for targeted mutagenesis is done systematically, or determined from studies whereby panels of monoclonal antibodies against each factor are used to map regions of the cytokine that might be exposed after binding of the cytokine to the α receptor component alone, or to the αβ1 heterodimeric soluble receptors described above. Similarly, chemical modification or limited proteolysis of the cytokine alone or in a complex bound to the α receptor component or the αβ1 heterodimeric soluble receptors described above, followed by analysis of the protected and exposed regions could reveal potential β2 binding sites.

Assays for identifying CNTF or IL-6 mutants with the desired properties involve the ability to block with high affinity the action of IL-6 or CNTF on appropriately responsive cell lines [Davis, et al., Science 259:1736–1739 (1993); Murakami et al., Proc. Natl. Acad. Sci. USA 88:11349–11353 (1991)]. Such assays include cell proliferation, survival, or DNA synthesis driven by CNTF or IL-6, or the construction of cell lines where binding of factor induces production of reporters such as CAT or β-galactosidase [Savino, et al., Proc. Natl. Acad. Sci. USA 90:4067–4071 (1993)].

Alternatively, the properties of various mutants may be assessed with a receptor-based assay. One such assay consists of screening mutants for their ability to bind the sRα:β1 receptor heterodimers described above using epitope-tagged [Davis et al., Science 253:59–63 (1991)] sRα:β1 reagents. Furthermore, one can probe for the presence or absence of the β2 site by assessing whether an epitope-tagged soluble β2 reagent will bind to the cytokine in the presence of the α:β1 heterodimer. For example, CNTF only binds to LIFRβ (the β2 component) in the presence of both CNTFRα and gp130 [Davis, et al. Science 260:1805–1808 (1993); Stahl, et al. J. Biol. Chem. 268:7628–7631 (1993)]. Thus a soluble LIFRβ reagent would only bind to CNTF in the presence of the soluble sRα:β1 dimer sCNTFRα:β1. For IL-6, the sRα:β1 reagent would be IL- 6Rα:β1, and the probe for the β2 site would be epitope-tagged sgp130. Thus β2- mutants of CNTF would be identified as those that bound the sRα:β1 reagent, demonstrating that the α and β1 site of the cytokine were intact, yet failed to bind the β2 reagent.

In addition, the present invention provides for methods of detecting or measuring the activity of potential β2- mutants by measuring the phosphorylation of a β-receptor component or a signal transduction component selected from the group consisting of Jak1, Jak2 and Tyk2 or any other signal transduction component, such as the CLIPs, that are determined to be phosphorylated in response to a member of the CNTF family of cytokines.

A cell that expresses the signal transduction component(s) described herein may either do so naturally or be genetically engineered to do so. For example, Jak1 and Tyk-2-encoding nucleic acid sequences obtained as described in Velazquez, et al., Cell, Vol. 70:313–322 (1992), may be introduced into a cell by transduction, transfection, microinjection, electroporation, via a transgenic animal, etc., using any known method known in the art.

According to the invention, cells are exposed to a potential antagonist and the tyrosine phosphorylation of either the β-component(s) or the signal transduction component(s) are compared to the tyrosine phosphorylation of the same component(s) in the absence of the potential antagonist.

In another embodiment of the invention, the tyrosine phosphorylation that results from contacting the above cells with the potential antagonist is compared to the tyrosine phosphorylation of the same cells exposed to the parental CNTF family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF. Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor.

In another embodiment of the invention the above approaches are used to develop a method for screening for small molecule antagonists that act at various steps in the process of ligand binding, receptor complex formation, and subsequent signal transduction. Molecules that potentially interfere with ligand-receptor interactions are screened by assessing interference of complex formation between the soluble receptors and ligand as described above. Alternatively, cell-based assays in which IL-6 or CNTF induce response of a reporter gene are screened against libraries of small molecules or natural products to identify potential antagonists. Those molecules showing antagonist activity are rescreened on cell-based assays responding to other factors (such as GMCSF or factors like Neurotrophin-3 that activate receptor tyrosine kinases) to evaluate their specificity against the CNTF/IL- 6/OSM/LIF family of factors. Such cell-based screens are used to identify antagonists that inhibit any of numerous targets in the signal transduction process.

In one such assay system, the specific target for antagonists is the interaction of the Jak/Tyk family of kinases [Firmbach-Kraft, Oncogene 5:1329–1336 (1990); Wilks, et al., Mol. Cell. Biol. 11:2057–2065 (1991)] with the receptor β subunits. As described above, LIFRβ and gp130 preassociate with members of the Jak/Tyk family of cytoplasmic protein tyrosine kinases, which become activated in response to ligand-induced β component dimerization (Stahl, et al. Science (submitted; 1993). Thus small molecules that could enter the cell cytoplasm and disrupt the interaction between the β component and the Jak/Tyk kinase could potentially block all subsequent intracellular signaling. Such activity could be screened with an in vitro scheme that assessed the ability of small molecules to block the interaction between the relevant binding domains of purified β component and Jak/Tyk kinase. Alternatively, one could easily screen for molecules that could inhibit a yeast-based assay of β component binding to Jak/Tyk kinases using the two-hybrid interaction system [Chien, et al., Proc. Natl. Acad. Sci. 88:9578–9582 (1991)]. In such a system, the interaction between two proteins (β component and Jak/Tyk kinase or relevant domains thereof in this example) induces production of a convenient marker such as β-galactosidase. Collections of small molecules are tested for their ability to disrupt the desired interaction without inhibiting the interaction between two control proteins. The advantage of this screen would be the requirement that the test compounds enter the cell before inhibiting the interaction between the β component and the Jak/Tyk kinase.

The CNTF family antagonists described herein either bind to, or compete with the cytokines CNTF and IL-6. Accordingly, they are useful for treating diseases or disorders mediated by CNTF or IL-6. For example, therapeutic uses of IL-6 antagonists would include the following:

1) In osteoporosis, which can be exacerbated by lowering of estrogen levels in post-menopausal women or through ovariectomy, IL-6 appears to be a critical mediator of osteoclastogenesis, leading to bone resorption [Horowitz, Science 260:626–627 (1993); Jilka, et al., Science 257:88–91 (1992)]. Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts [Jilka, et al. Science 257:88–91 (1992)]. While estrogen replacement therapy is also used, there appear to be side effects that may include increased risk of endometrial and breast cancer. Thus, IL-6 antagonists as described herein would be more specific to reduce osteoclastogenesis to normal levels.

2) IL-6 appears to be directly involved in multiple myeloma by acting in either an autocrine or paracrine fashion to promote tumor formation [van Oers, et al., Ann Hematol. 66:219–223 (1993)]. Furthermore, the elevated IL-6 levels create undesirable secondary effects such as bone resorption, hypercalcemia, and cachexia; in limited studies function-blocking antibodies to IL-6 or IL-6Rα have some efficacy [Klein, et al., Blood 78:1198–1204 (1991); Suzuki, et al., Eur. J. Immunol. 22:1989–1993 (1992)]. Therefore, IL-6 antagonists as described herein would be beneficial for both the secondary effects as well as for inhibiting tumor growth.

3) IL-6 may be a mediator of tumor necrosis factor (TNF) that leads to cachexia associated with AIDS and cancer [Strassmann, et al., J. Clin. Invest. 89:1681–1684 (1992)], perhaps by reducing lipoprotein lipase activity in adipose tissue [Greenberg, et al., Cancer Research 52:4113–4116 (1992)]. Accordingly, antagonists described herein would be useful in alleviating or reducing cachexia in such patients.

Effective doses useful for treating these or other CNTF family related diseases or disorders may be determined using methods known to one skilled in the art [see, for example, Fingl, et al., The Pharmacological Basis of Therapeutics, Goodman and Gilman, eds. Macmillan Publishing Co., New York, pp. 1–46 ((1975)]. Pharmaceutical compositions for use according to the invention include the antagonists described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation (including antagonist expressing cells) prior to administration in vivo. For example, the pharmaceutical composition may comprise one or more of the antagonists in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

EXAMPLE 1: CNTF COMPETES WITH IL-6 FOR BINDING TO GP130

Materials and Methods

Materials. A clone of PC12 cells that respond to IL-6 (PC12D) was obtained from DNAX. Rat CNTF was prepared as described [Masiakowski, et al., J. Neurochem. 57:1003–10012 (1991)]. IL-6 and sIL-6R were purchased from R & D Systems. Antisera was raised in rabbits against a peptide derived from a region near the C-terminus of gp130 (sequence: CGTEGQVERFETVGME) [Seq. ID No.:2] by the method described (Stahl, et al. J. Biol. Chem. 268:7628–7631 (1993). Antiphosphotyrosine monoclonal 4G10 was purchased from UBI, and reagents for ECL from Amersham.

Signal Transduction Assays. Plates (10 cm) of PC12D were starved in serum-free medium (RPMI 1640+ glutamine) for 1 hour, then incubated with IL-6 (50 ng/mL)+ sIL-6R (1 μg/mL) in the presence or absence of added rat CNTF at the indicated concentrations for 5 minutes at 37° C. Samples were then subjected to anti-gp130 immunoprecipitation, SDS PAGE, and anti-phosphotyrosine immunoblotting as described (Stahl, et al. J. Biol. Chem. 268:7628–7631 (1993).

RESULTS

Figure 2:
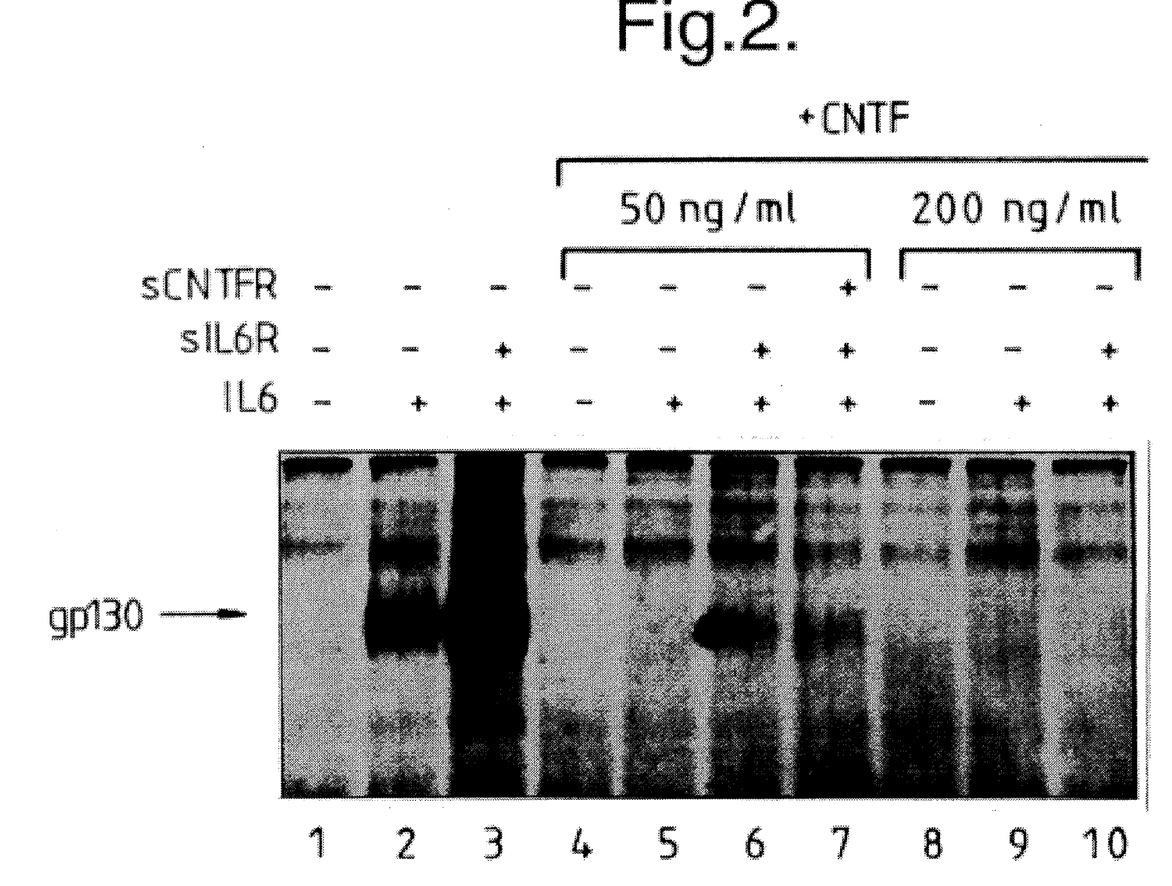
FIG. 2: CNTF inhibits IL-6 responses in a PC12 cell line (called PC12D) that expresses IL6R$\alpha$, gp130, CNTFR$\alpha$, but not LIFR$\beta$. Serum-deprived PC12D cells were incubated+ IL-6 (50 ng/mL) in the presence or absence of CNTF as indicated. Some plates also received soluble IL6R$\alpha$ (1 mg/mL) or soluble CNTFR$\alpha$ (1 mg/mL) as indicated. Cell lysates were subjected to immunoprecipitation with anti-gp 130 and immunoblotted with anti-phosphotyrosine. Tyrosine phosphorylation of gp130 is indicative of IL-6 induced activation of the IL-6 receptor system, which is blocked upon coaddition of CNTF.

The ability of CNTF to block IL-6 responses was measured using a PC12 cell line (called PC12D) that expresses IL-6Rα, gp130, and CNTFRα, but not LIFRβ. As one would predict, these cells respond to IL-6, but not to CNTF (FIG. 2) since LIFRβ is a required component for CNTF signal transduction [Davis, et al., Science 260: 59–63 (1993)]. In accordance with results on other cell lines [Ip, et al., Cell 69:1121–1132 (1992)], PC12D cells give tyrosine phosphorylation of gp130 (as well as a variety of other proteins called CLIPs)in response to 2 nM IL-6 (FIG. 2). Addition of recombinant soluble IL-6Rα (sIL-6Rα) enhances the level of gp130 tyrosine phosphorylation, as has been reported in some other systems [(Taga, et al., Cell 58:573–581 (1989)]. However, addition of 2 nM CNTF simultaneously with IL-6 severely diminishes the tyrosine phosphorylation of gp130. Although a slight gp130 phosphorylation response remains in the presence of CNTF, IL-6, and sIL-6Rα, it is eliminated if the CNTF concentration is increased fourfold to 8 nM. Thus, in IL-6 responsive cells that contain CNTFRα but no LIFRβ, CNTF is a rather potent antagonist of IL-6 action.

EXAMPLE 2. BINDING OF CNTF TO THE CNTFRα:β

Materials and Methods

Scatchard Analysis of CNTF Binding, $^{125}$I-CNTF was prepared and purified as described [Stahl et al. JBC 268:7628–7631 (1993)]. Saturation binding studies were carried out in PC12 cells, using concentrations of $^{125}$I-CNTF ranging from 20 pM to 10 nM. Binding was performed directly on a monolayer of cells. Medium was removed from wells and cells were washed once with assay buffer consisting of phosphate buffered saline (PBS; pH 7.4), 0.1 mM bacitracin, 1 mM PMSF, 1 µg/ml leupeptin, and 1 mg/ml BSA. Cells were incubated in $^{251}$I-CNTF for 2 hours at room temperature, followed by 2 quick washes with assay buffer. Cells were lysed with PBS containing 1% SDS and counted in a Packard Gamma Counter at 90–95% efficiency. Nonspecific binding was defined by the presence of 100-fold excess of unlabelled CNTF. Specific binding ranged from 70% to 95%.

RESULTS

Figure 3:
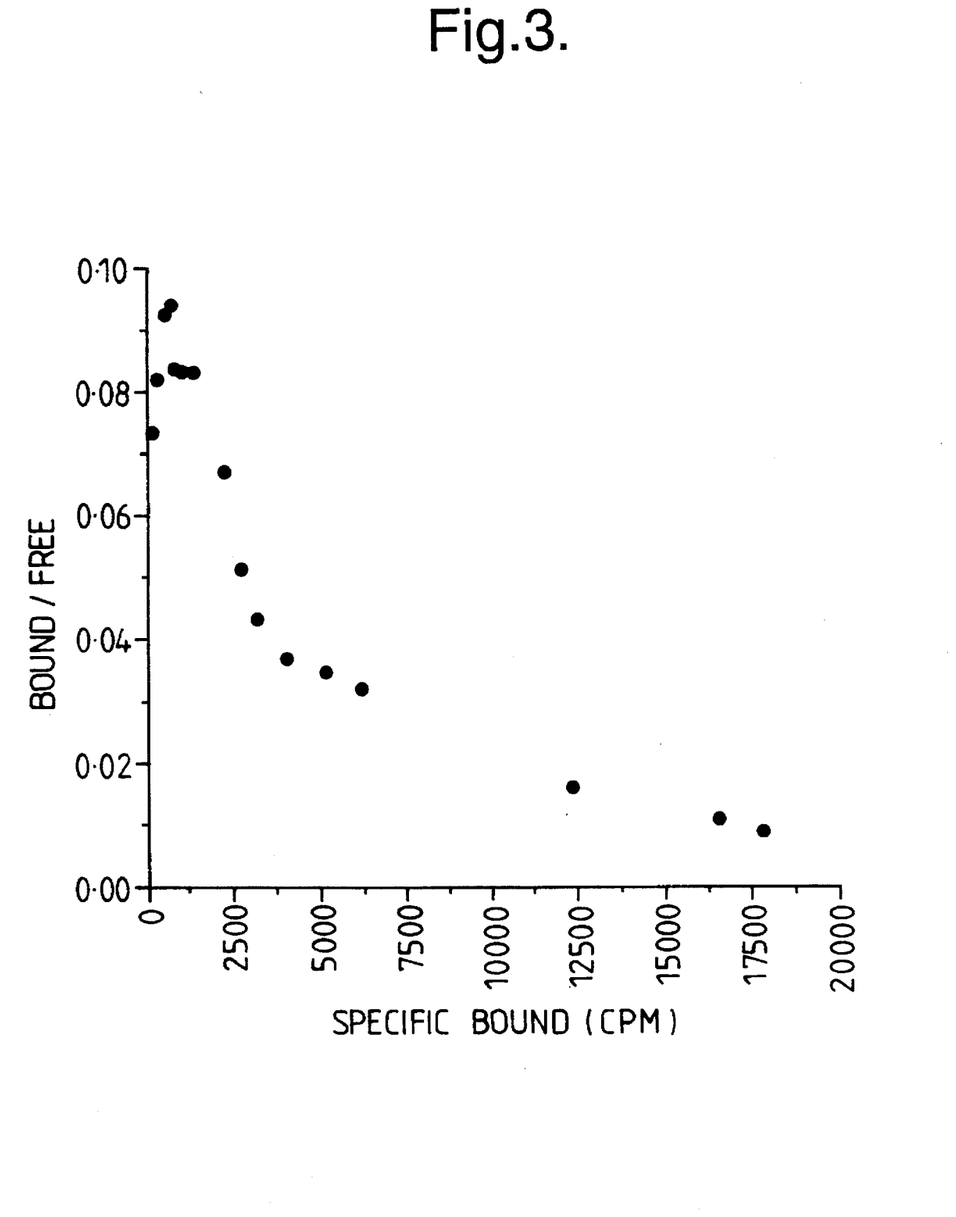
FIG. 3: Scatchard analysis of iodinated CNTF binding on PC12D cells. PC12D cells were incubated with various concentrations of iodinated CNTF in the presence or absence of excess non-radioactive competitor to determine the specific binding. The figure shows a Scatchard plot of the amount of iodinated CNTF specifically bound, and gives data consistent with two binding sites with dissociation constants of 9 pM and 3.4 nM.

The equilibrium constant for binding of CNTF to CNTFRα:β1 was estimated from Scatchard analysis of iodinated CNTF binding on PC12D cells (FIG. 3). The data is consistent with a 2 site fit having dissociation constants of 9 pM and 3.4 nM. The low affinity site corresponds to interaction of CNTF with CNTFRα, which has a Kd near 3 nM [(Panayotatos, et al., J. Biol. Chem. 268:19000–19003 (1993)]. We interpret the high affinity complex as the intermediate containing CNTF, CNTFRα, and gp130. A Ewing sarcoma cell line (EW-1) which does contain CNTFRα, gp130, and LIFRβ, and therefore gives robust tyrosine phosphorylation in response to CNTF, displays a very similar two site fit with dissociation constants of 1 nM and 10 pM (Wong, et al., unpublished data). Thus it is apparent that CNTF binds with equally high affinity to a complex containing only CNTFRα and gp130, as it does to a complex which additionally contains LIFRβ, thus demonstrating the feasibility of creating the sRα:β antagonists described herein.

We claim:

1. An IL-6 antagonist, capable of binding IL-6 to form a nonfunctional complex, comprising:

a) soluble IL-6Rα; and
b) the extracellular domain of gp130.

2. A CNTF antagonist, capable of binding CNTF to form a nonfunctional complex, comprising:

a) soluble CNTFRα; and
b) the extracellular domain of gp130.

* * * * *